United States Patent
Lee et al.

(10) Patent No.: US 9,250,177 B2
(45) Date of Patent: Feb. 2, 2016

(54) READER FOR URINE ANALYSIS

(75) Inventors: Kyu-Dae Lee, Hanam-si (KR);
Jae-Hoon Song, Daegu (KR); In-Hyuk Cha, Seoul (KR)

(73) Assignee: DAE KYOUNG IND. CO., LTD. (KR)

( * ) Notice: Subject to any disclaimer, the term of this patent is extended or adjusted under 35 U.S.C. 154(b) by 0 days.

(21) Appl. No.: 14/119,240

(22) PCT Filed: Sep. 8, 2011

(86) PCT No.: PCT/KR2011/006646
§ 371 (c)(1),
(2), (4) Date: Nov. 21, 2013

(87) PCT Pub. No.: WO2013/015483
PCT Pub. Date: Jan. 31, 2013

(65) Prior Publication Data
US 2014/0185050 A1 Jul. 3, 2014

(30) Foreign Application Priority Data
Jul. 22, 2011 (KR) .................. 10-2011-0072852

(51) Int. Cl.
| G01N 21/55 | (2014.01) |
| G01N 21/17 | (2006.01) |
| G01N 21/47 | (2006.01) |
| G01N 33/493 | (2006.01) |
| G01N 21/84 | (2006.01) |

(52) U.S. Cl.
CPC ............ *G01N 21/17* (2013.01); *G01N 21/4738* (2013.01); *G01N 21/55* (2013.01); *G01N 21/8483* (2013.01); *G01N 33/493* (2013.01)

(58) Field of Classification Search
None
See application file for complete search history.

(56) References Cited

U.S. PATENT DOCUMENTS

2006/0028648 A1 * 2/2006 Yao et al. ...................... 356/446

FOREIGN PATENT DOCUMENTS

| KR | 100129488 B | 8/1998 |
| KR | 1020100073061 A | 7/2010 |
| KR | 1020110027013 A | 3/2011 |
| KR | 1020110027026 A | 3/2011 |

OTHER PUBLICATIONS

International Search Report of PCT/KR2011/006646 dated Jun. 21, 2012.
Certificate of attendance and brochure. 2011 International Health Industry Exhibition.
Certificate of attendance and brochure. 2011 Kimes.
Year 2012 Product Brochure.

* cited by examiner

*Primary Examiner* — Gregory J Toatley
*Assistant Examiner* — Amanda Merlino
(74) *Attorney, Agent, or Firm* — Lee Patent International

(57) ABSTRACT

A urine analysis device includes a light emitting part, a light receiving part and a control part. The light emitting part includes a plurality of light emitting diodes. The light emitting diodes provide a light to an inspected object. The inspected object has a plurality of inspected areas. The light receiving part receives the light reflected by the inspected object. The control part drives the light emitting part and receives an electric signal from the light receiving part.

1 Claim, 5 Drawing Sheets

READER FOR URINE ANALYSIS

PRIORITY STATEMENT

This application claims priority under 35 U.S.C. §119 to Korean Patent Application No. 2011-0072852, filed on Jul. 22, 2011 in the Korean Intellectual Property Office (KIPO), the contents of which are herein incorporated by reference in their entireties.

BACKGROUND OF THE INVENTION

1. Field of the Invention

Example embodiments of the present invention relate to a urine analysis device. More particularly, example embodiments of the present invention relate to a digital and portable urine analysis device.

2. Description of the Related Art

Generally, a urine analysis device used in a hospital for a diagnosis is very expensive and is too big to be personally carried.

Recently, a portable urine analysis device with a small size has been developed and in the portable urine analysis device, urine is dropped on a strip so as to diagnose proteinuria, glucosuria, occult blood and so on.

In the portable urine analysis device, a semi-quantitative value may be read due to a variation of color data which is detected on the strip within one minute. Thus, a transition of proteinuria, glucosuria, occult blood and so on of a patient is continuously monitored, and thus an emergent treatment may be performed in an abnormal state of the patient. Accordingly, the portable urine analysis device with a small size is very useful.

Generally, the portable urine analysis device includes a three-color light emitting diode (LED), an optical fiber waveguide and a photo-detector. The light emitting diode emits the colors corresponding to diagnosis items of the strip to the photo-detector though the optical fiber waveguide. Thus, the photo-detector may read diseases based on the light receiving from the diagnosis items of the strip.

However, in the portable urine analysis device uses a single light emitting diode to detect a plurality of the diagnosis items of the strip through the optical fiber waveguide, so that the light reflected by the diagnosis item of the strip may be received by a photo-detector adjacent to the photo-detector corresponding to the diagnosis item. Accordingly, the portable urine analysis device may incorrectly diagnose the disease.

SUMMARY OF THE INVENTION

Example embodiments of the present invention provide a urine analysis device capable of diagnose a disease more correctly.

In an example urine analysis device according to the present invention, the urine analysis device includes a light emitting part, a light receiving part and a control part. The light emitting part includes a plurality of light emitting diodes. The light emitting diodes provide a light to an inspected object. The inspected object has a plurality of inspected areas. The light receiving part receives the light reflected by the inspected object. The control part drives the light emitting part and receives an electric signal from the light receiving part.

In the example embodiment, the light emitting diodes may include a red light emitting diode (LED), a green LED and a blue LED.

In the example embodiment, the control part may include a driving part, an amplifying part, an analog-to-digital converter and an analyzing part. The driving part may sequentially drive the light emitting diodes. The amplifying part may amplify the electric signal. The analog-to-digital converter may convert the amplified electric signal to a digital signal. The analyzing part may analyze the digital signal.

In the example embodiment, the driving part may sequentially drive the light emitting diodes group by group.

In the example embodiment, the receiving part may be arranged parallel with the light emitting part in a plan view, and may include a plurality of photo-detectors respectively corresponding to the light emitting diodes.

In the example embodiment, the urine analysis device may further include a supporting plate supporting the inspected object, and arranged in an area between the light emitting part and the light receiving part.

According to the present example embodiments, the urine analysis device includes a plurality of light emitting diodes to omit an additional optical waveguide to guide a light.

In addition, the light emitting diodes are sequentially driven to block interference due to the light reflected by adjacent light emitting diode except for the driven light emitting diode in adjacent detecting area.

In addition, the light emitting devices are driven in a group to block the interference due to the light reflected by the adjacent light emitting diode except for the driven light emitting diode in adjacent detecting area.

Accordingly, the urine analysis device may be operated more correctly.

BRIEF DESCRIPTION OF THE DRAWINGS

The above and other features and advantages of the present invention will become more apparent by describing in detailed example embodiments thereof with reference to the accompanying drawings, in which.

DETAILED DESCRIPTION OF THE INVENTION

Hereinafter, the present invention will be explained in detail with reference to the accompanying drawings.

Figure 1:
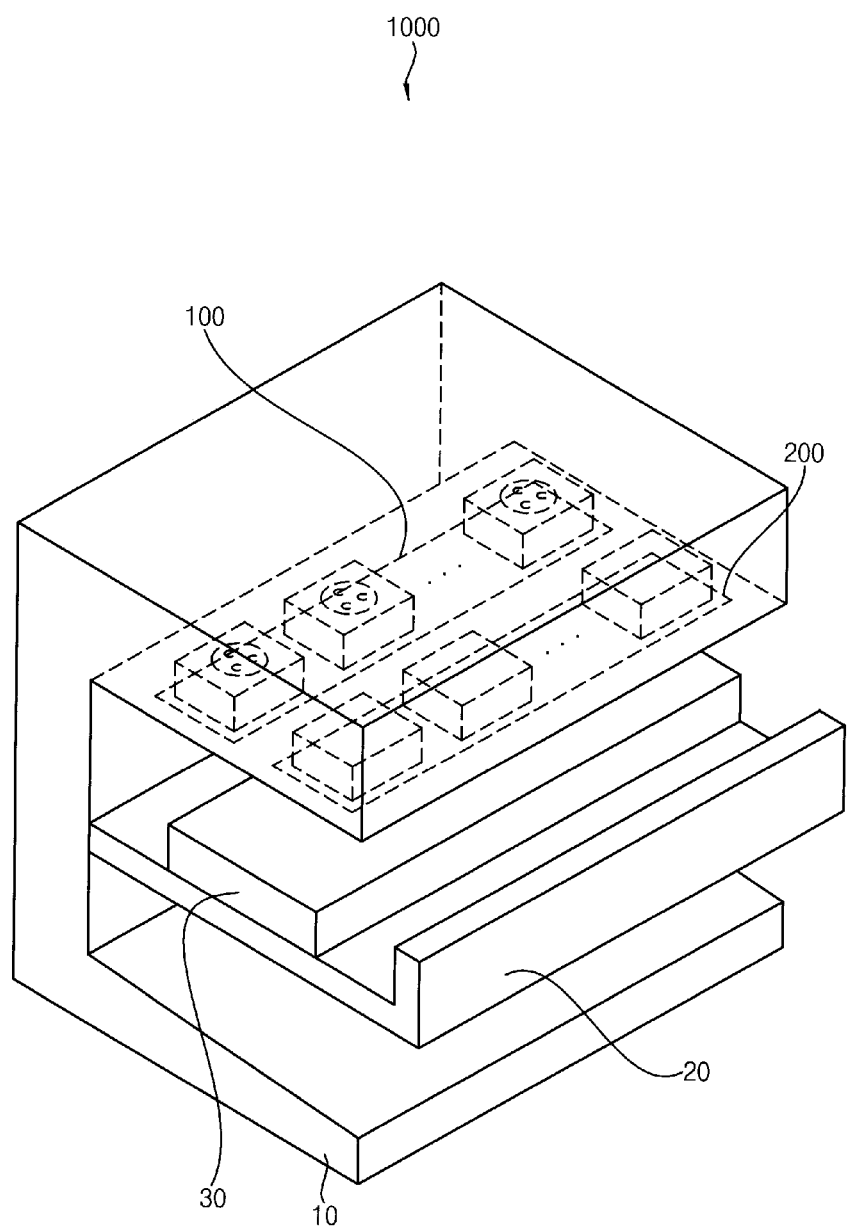
FIG. 1 is a prospective view illustrating a urine analysis device according to an example embodiment of the present invention.
Figure 2:
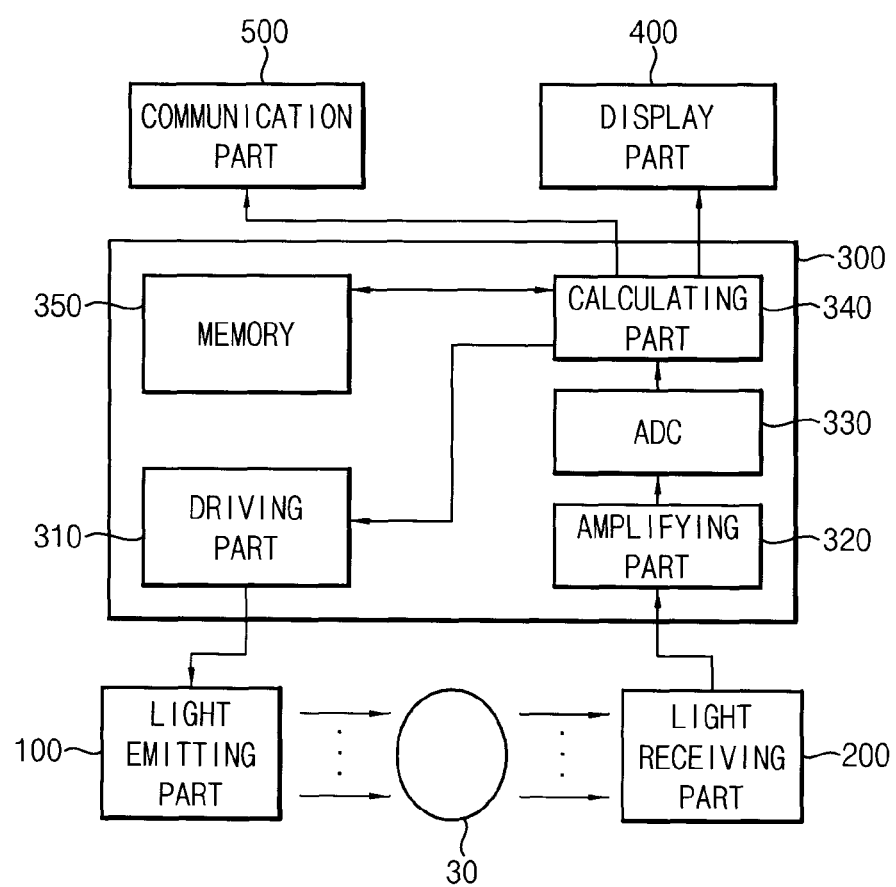
FIG. 2 is a block diagram of the urine analysis device of FIG. 1.

FIG. 1 is a prospective view illustrating a urine analysis device according to an example embodiment of the present invention. FIG. 2 is a block diagram of the urine analysis device of FIG. 1.

Referring to FIGS. 1 and 2, the urine analysis device 1000 according to the present example embodiment includes a housing 10, a supporting plate 20, a light emitting part 100, a light receiving part 200, a control part 300 and a display part 400.

The housing 10 has a receiving space in which the light emitting part 100, the light receiving part 200, the control part 300 and the display part 400 are received. The housing 10 may have a 'U-like' shape in a cross-sectional view. The housing 10 includes an upper portion receiving the light emitting part 100 and the light receiving part 200, a lower portion facing the upper portion and having contact with a ground, and a connection portion connecting the upper portion with the lower portion.

The supporting part 20 supports an inspected object 30 which is inspected and diagnosed by the urine analysis device 1000, and is disposed in a space between the upper and lower portions. For example, the supporting part 20 may be inserted to and removed from the space between the upper and lower portions. The supporting part 20 is disposed in the space between the upper and lower portions, and at the same time, the urin analysis device 1000 is turned on. The inspected object 30 may be a strip chip or a bio-chip having a plurality of areas respectively assigned to inspected items (hereinafter, an inspected area).

Alternatively, the urine analysis device 1000 may be turned on via an additional switch.

The light emitting part 100 may include a plurality of light emitting diodes (LEDs) 110. The LEDs 110 may include a red LED, a green LED and a blue LED. The red, green and blue LEDs are switched so as to be discontinuously controlled. Thus, the red, green and blue LEDs respectively emit red, green and blue colors.

The light receiving part 200 includes a plurality of photo-detectors 210. Each of the photo-detectors 210 may be a silicon-based sensor such as a silicon photo diode, a photo triode and so on. The light receiving part 200 receives the light which is provided by the light emitting part 100 and is reflected by the inspected object 30, and converts the light into an electric signal to provide the electric signal to an amplifying part 320 of the control part 300.

The light receiving part 200 is arranged parallel with the light emitting part 100 in a same plane. For example, the light receiving part 200 and the light emitting part 100 are both in the upper portion of the housing 10. The supporting part 20 is disposed under both the light receiving part 200 and the light emitting part 100, and is disposed in a space between the light receiving part 200 and the light emitting part 100 in a plan view.

The control part 300 includes a driving part 310, an amplifying part 320, an analog-to-digital converter (ADC) 330, an analyzing part 340 and a memory 350.

The driving part 310 drives the light emitting part 100, when the supporting plate 20 is set up to the housing 10 and the urine analysis device 1000 is turned on. The driving part 310 sequentially turns on the LEDs 110. Thus, the LEDs 110 sequentially and respectively provide the light to the inspected areas of the inspected object 30. For example, a first LED provides the light to a first inspected area of the inspected object, and then a second LED provides the light to a second inspected area of the inspected object, and so on.

Alternatively, the driving part 310 may sequentially turn on the LEDs group by group. Thus, the LEDs 110 may sequentially and respectively provide the light to the inspected areas of the inspected object 30 group by group. For example, a first group of LEDs provides the light to a first group of inspected areas of the inspected object, and then a second group of LEDs provides the light to a second group of inspected areas of the inspected object, and so on.

The amplifying part 320 receives the electric signal of the light reflected by the inspected object 30, and amplifies the electric signal to provide the amplified electric signal to the ADC 330.

The ADC 330 receives the amplified electric signal, and converts the amplified electric signal to a digital signal to provide the digital signal to the analyzing part 340.

The analyzing part 340 receives and analyzes the digital signal to provide the digital signal to the display part 400. For example, the analyzing part 340 analyzes the digital signal based on color coordinates such as a look-up table which is provided from the memory 350. In addition, the analyzing part 340 may have analyzed results or data to be stored in the memory 350.

The memory 350 provides the color coordinates used for analyzing the inspected object 30, and stores the analyzed results or data.

The display part 400 displays the analyzed results or data, and may be a monitor displaying an image or a printer.

The urine analysis device 1000 may further include a communication part 500 providing the analyzed results or data to outer terminal, and a correction part (not shown) correcting the analyzed results or data.

Figure 3:
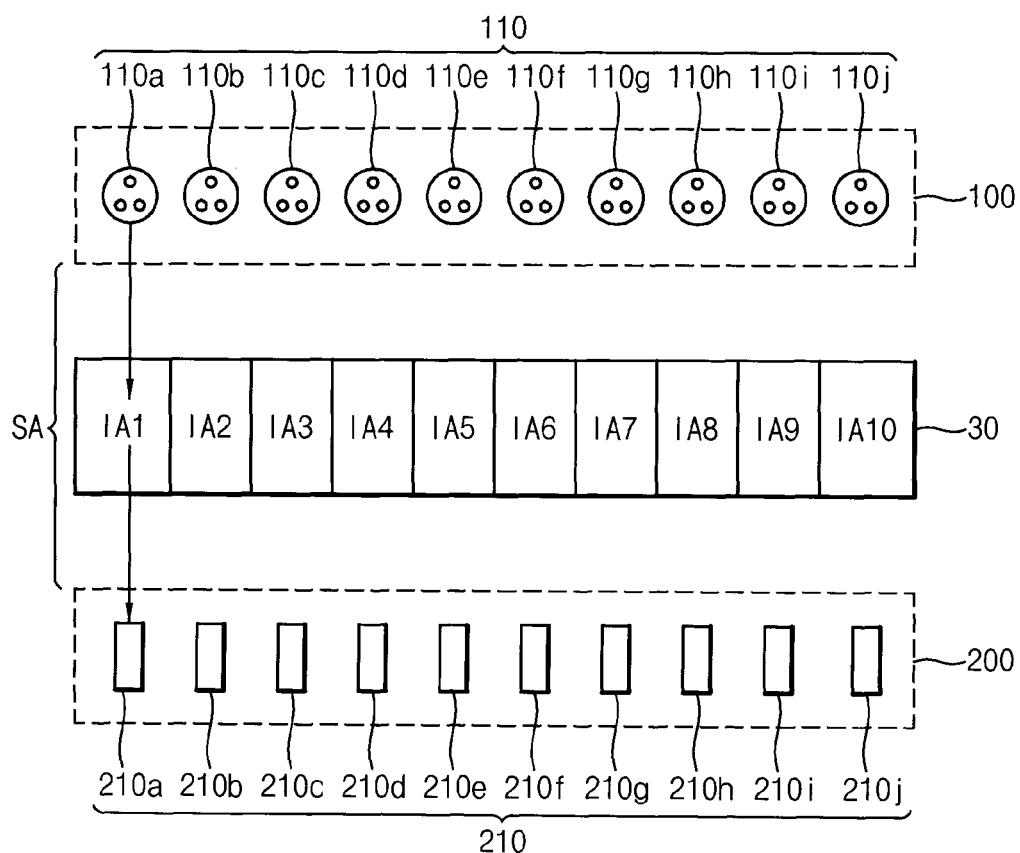
FIG. 3 is a diagram for explaining a driving operation of light emitting diodes and photo-detectors in FIG. 1.

FIG. 3 is a diagram for explaining a driving operation of light emitting diodes and photodetectors in FIG. 1.

Referring to FIG. 3, the light emitting part 100, for example, may include first to tenth LEDs 110a, 110b, . . . , 110j which are arranged in a line as illustrated.

The light receiving part 200, for example, may include first to tenth photo-detectors 210a, 210b, . . . , 210j which respectively correspond to the first to tenth LEDs 110a, 110b, . . . , 110j. The first to tenth photo-detectors 210a, 210b, . . . , 210j are arranged in a line, and each is spaced apart from each of the first to tenth LEDs 110a, 110b, . . . , 110j by a predetermined distance.

The inspected object 30, for example, may be divided into first to tenth inspected areas IA1, IA2, . . . , IA10. The inspected object 30 is disposed in an area SA between the light emitting part 100 and the light receiving part 200 in a plan view. For example, each of the first to tenth inspected areas IA1, IA2, . . . , IA10 is disposed in the area SA between each of the first to tenth LEDs 110a, 110b, . . . , 110j and each of the first to tenth photo-detectors 210a, 210b, . . . , 210j.

The first to tenth inspected areas IA1, IA2, . . . , IA10 are partially overlapped with each of the light emitting part 100 and the light receiving part 200.

The first to tenth LEDs 110a, 110b, . . . , 110j are sequentially driven.

For example, the first LED 110a is driven, and thus the light emitted from the first LED 110a is reflected in the first inspected area IA1 to be provided to the first photo-detector 210a. Then, the second LED 110b is driven, and thus the light emitted from the second LED 110b is reflected in the second inspected area IA2 to be provided to the second photo-detector 210b. Likewise, the third to tenth LEDs 110c, . . . , 110j are operated.

Thus, when the first LED 110a is driven, the second to tenth LEDs 110b, . . . , 110j are not driven, and thus the first photo-detector 210a is not affected by the photo-detectors except for the first LED 110a.

According to the present example embodiment, the urine analysis device 1000 includes a plurality of LEDs 110, and thus the photo-detector 210 may receive the light from the LED 110 more correctly and more efficiently without an additional waveguide.

In addition, the LEDs 110 are sequentially driven and the photo-detectors 210 sequentially receives the light, and thus the photo-detector 210 may receive the light from the LED 110 more correctly and more efficiently without an additional sidewall through which adjacent light is blocked in the conventional urine analysis device.

Figure 4:
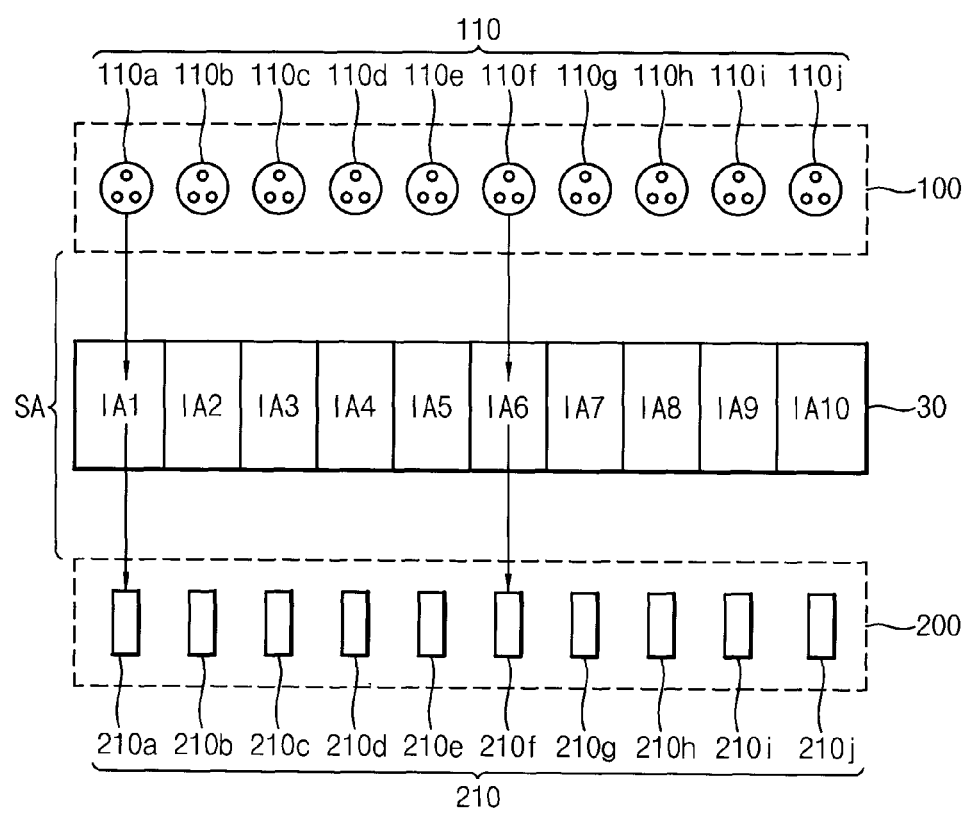
FIG. 4 is a diagram for explaining a driving operation of light emitting diodes and photo-detectors of a urine analysis device according to another example embodiment of the present invention.

FIG. 4 is a diagram for explaining a driving operation of light emitting diodes and photo-detectors of a urine analysis device according to another example embodiment of the present invention.

The urine analysis device according to the present example embodiment is substantially same as the urine analysis device according to the previous example embodiment in FIGS. 1 to 3, except for a driving of LEDs and photo-detectors, and thus same reference numerals are used and any further repetitive explanation are omitted.

Referring to FIG. 4, first to tenth LEDs 110a, 110b, ..., 110j according to the present example embodiment are drive group by group. For example, the first and sixth LEDs 110a and 110f are grouped to be a first group, the second and seventh LEDs 110b and 110g are grouped to be a second group, the third and the eighth LEDs 110c and 110h are grouped to be a third group, the fourth and the ninth LEDs 110d and 110i are grouped to be a fourth group, and the fifth and the tenth LEDs 110e and 110j are grouped to be a fifth group.

The first to fifth groups are sequentially driven.

For example, the first and sixth LEDs 110a and 110f of the first group are driven, and thus the light emitted from the first and sixth LEDs 110a and 110f are respectively reflected in the first and sixth inspected areas IA1 and IA6 to be respectively provided to the first and sixth photo-detectors 210a and 210f.

When the first group is driven, the photo-detectors except for the first and sixth photo-diodes 210a and 210f may have a function of the sidewall in the conventional urine analysis device.

Then, the second and seventh LEDs 110b and 110g of the second group are driven, and thus the light emitted from the second and seventh LEDs 110b and 110g are respectively reflected in the second and seventh inspected areas IA2 and IA7 to be respectively provided to the second and seventh photo-detectors 210b and 210g.

When the second group is driven, the photo-detectors except for the second and seventh photo-diodes 210b and 210g may have a function of the sidewall in the conventional urine analysis device.

Likewise, the third to fifth groups may be operated in a substantially same manner. According to the present example embodiment, the urine analysis device 1000 drives the plurality of LEDs 110 group by group, and thus the photo-detector 210 may receive the light from the LED 110 more correctly and more efficiently without an additional sidewall through which adjacent light is blocked in the conventional urine analysis device.

Figure 5:
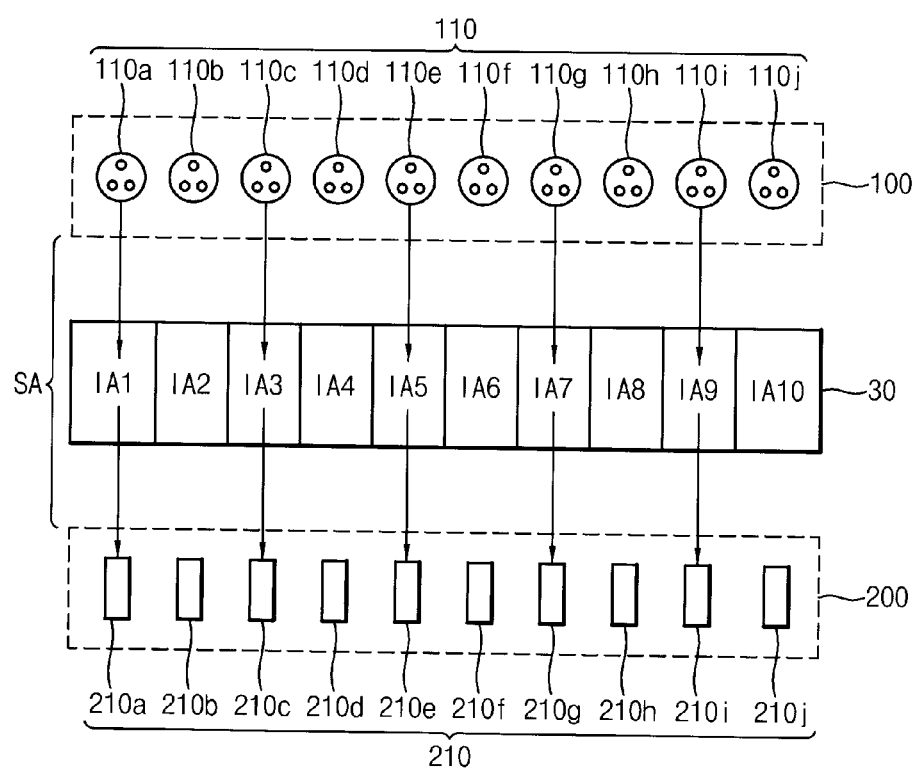
FIG. 5 is a diagram for explaining a driving operation of light emitting diodes and photo-detectors of a urine analysis device according to still another example embodiment of the present invention.

FIG. 5 is a diagram for explaining a driving operation of light emitting diodes and photo-detectors of a urine analysis device according to still another example embodiment of the present invention.

The urine analysis device according to the present example embodiment is substantially same as the urine analysis device according to the previous example embodiment in FIGS. 1 to 3, except for a driving of LEDs and photo-detectors, and thus same reference numerals are used and any further repetitive explanation are omitted.

Referring to FIG. 5, first to tenth LEDs 110a, 110b, ..., 110j according to the present example embodiment are drive group by group. For example, the first, third, fifth, seventh and ninth LEDs 110a, 110c, 110e, 110g and 110i are grouped to be a first group, and the second, fourth, sixth, eighth and tenth LEDs 110b, 110d, 110f, 110h and 110j are grouped to be a second group.

The first and second groups are alternately driven.

For example, the first, third, fifth, seventh and ninth LEDs 110a, 110c, 110e, 110g and 110i of the first group are driven, and thus the light emitted from the first, third, fifth, seventh and ninth LEDs 110a, 110c, 110e, 110g and 110i are respectively reflected in the first, third, fifth, seventh and ninth inspected areas IA1, IA3, IA5, IA7 and IA9 to be respectively provided to the first, third, fifth, seventh and ninth photo-detectors 210a, 210c, 210e, 210g and 210i which respectively correspond to the first, third, fifth, seventh and ninth LEDs 110a, 110c, 110e, 110g and 110i.

When the first group is driven, the even-numbered second, fourth, sixth, eighth and tenth photo-diodes 210b, 210d, 210f, 210h and 210j respectively disposed between the odd-numbered first, third, fifth, seventh and ninth LEDs 210a, 210c, 210e, 210g and 210i may have a function of the sidewall in the conventional urine analysis device.

Then, the second, fourth, sixth, eighth and tenth LEDs 110b, 110d, 110f, 110h and 110j of the second group are driven, and thus the light emitted from the second, fourth, sixth, eighth and tenth LEDs 110b, 110d, 110f, 110h and 110j are respectively reflected in the second, fourth, sixth, eighth and tenth inspected areas IA2, IA4, IA6, IA8 and IA10 to be respectively provided to the second, fourth, sixth, eighth and tenth photo-detectors 210b, 210d, 210f, 210h and 210j which respectively correspond to the second, fourth, sixth, eighth and tenth LEDs 110b, 110d, 110f, 110h and 110j.

When the second group is driven, the odd-numbered first, third, fifth, seventh and ninth LEDs 210a, 210c, 210e, 210g and 210i respectively disposed between the even-numbered second, fourth, sixth, eighth and tenth photo-diodes 210b, 210d, 210f, 210h and 210j may have a function of the sidewall in the conventional urine analysis device.

Then, the first and second groups are sequentially driven again.

According to the present example embodiment, the urine analysis device 1000 drives the plurality of LEDs 110 group by group, and thus the photo-detector 210 may receive the light from the LED 110 more correctly and more efficiently without an additional sidewall through which adjacent light is blocked in the conventional urine analysis device.

According to the present example embodiment, the urine analysis device includes a plurality of light emitting diodes to omit an additional optical waveguide to guide a light.

In addition, the light emitting diodes are sequentially driven to block interference due to the light reflected by adjacent light emitting diode except for the driven light emitting diode in adjacent detecting area.

In addition, the light emitting devices are driven in a group to block the interference due to the light reflected by the adjacent light emitting diode except for the driven light emitting diode in adjacent detecting area.

Accordingly, the urine analysis device may be operated more correctly.

The foregoing is illustrative of the present invention and is not to be construed as limiting thereof. Although a few example embodiments of the present invention have been described, those skilled in the art will readily appreciate that many modifications are possible in the example embodiments without materially departing from the novel teachings and advantages of the present invention. Accordingly, all such modifications are intended to be included within the scope of the present invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific example embodiments disclosed, and that modifications to the disclosed example embodiments, as well as other example embodiments, are intended to be included within the scope of the appended claims. The present invention is defined by the following claims, with equivalents of the claims to be included therein.

What is claimed is:

1. A urine analysis device comprising:
   a plurality of light emitting diodes providing a light to an inspected object that has a plurality of inspected areas;
   a plurality of photo-detectors respectively corresponding to the light emitting diodes, receiving the light reflected by the inspected object, and arranged parallel with the plurality of light emitting diodes in a plan view;
   a controller driving the plurality of light emitting diodes and receiving an electric signal from the plurality of photo-detectors;
   a supporting plate supporting the inspected object; and,
   a housing including an upper portion receiving the plurality of light emitting diodes and the plurality of photo-detectors and lower portion receiving the supporting plate;
   wherein the plurality of light emitting diodes are divided into a plurality of groups and are sequentially driven by group,
   wherein each of the group comprises the plurality of light emitting diodes disposed not adjacent to each other,
   wherein the plurality of light emitting diodes comprises a red light emitting diode (LED), a green LED and a blue LED,
   wherein the plurality of photo-detectors respectively corresponding to the un-driven light emitting diodes have a function of a sidewall,
   wherein the controller comprises, a driver sequentially driving the light emitting diodes, an amplifier amplifying the electric signal, an analog-to-digital converter converting the amplified electric signal to a digital signal, and an analyzer analyzing the digital signal,
   wherein the supporting plate is arranged in an area between the plurality of light emitting diodes and the plurality of photo-detectors.

* * * * *